(12) United States Patent
Johnson (10) Patent No.: US 6,256,096 B1
(45) Date of Patent: *Jul. 3, 2001

(54) FLOW CYTOMETRY APPARATUS AND METHOD

(75) Inventor: Paul E. Johnson, Laramie, WY (US)

(73) Assignee: SoftRay, Laramie, WY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/228,247

(22) Filed: Jan. 11, 1999

(51) Int. Cl.[7] .................................................. G01N 15/02

(52) U.S. Cl. ............................................................ 356/335

(58) Field of Search ..................................... 356/335–343, 356/73, 317, 39, 72

(56) References Cited

U.S. PATENT DOCUMENTS 5,444,527 * 8/1995 Kosaka ..................................... 356/73
5,674,743 * 10/1997 Ulmer ................................. 435/287.2

* cited by examiner

Primary Examiner—Frank G. Font
Assistant Examiner—Tu T. Nguyen
(74) Attorney, Agent, or Firm—Jennifer L. Bales; Macheledt Bales & Johnson LLP (57) ABSTRACT

A flow cytometer for detecting target particles such as microorganisms including biological cells and viruses as well as molecular species. The flow cytometer includes a detection system involving a CCD having a time delay integration capability to thereby increase the signal from the target particle and decrease the noise detected by the CCD. Calibration particles can be included in the sample stream of the flow cytometer for coordinating the readout of the CCD with the rate of flow of the sample stream to improve the detection capability of the CCD. Statistical analysis techniques can also be used to determine the rate of flow of target particles in the sample stream to thereby coordinate the readout rate of the CCD with the rate of flow of the target particles.

15 Claims, 3 Drawing Sheets

FLOW CYTOMETRY APPARATUS AND METHOD

BACKGROUND

1. Field of the Invention

This invention relates to flow cytometry and, more particularly, to an improved flow cytometry apparatus and method involving a novel time delayed integration of a charge coupled device in the detection apparatus for enhancing the signal-to-noise ratio.

2. The Prior Art

Cytometry is the measurement of the physical and/or chemical characteristics of biological cells. Since the technology of my novel discovery as disclosed and claimed herein can be adapted to other systems such as viruses and molecules as well as biological cells, I have adopted the term "cytometry" to refer to the detection of all of these species which, for the sake of convenience are referred to herein as "target particle(s)." Flow cytometry, as the name implies, involves the delivery of a flowing stream containing a sample having target particles therein to the detection region of a flow cytometer. The target particles in the detection region are irradiated using a laser to create an illumination phenomena by the target particles. The appropriate optics and detection electronics measure the light absorption; scattering; fluorescence; and/or spectral properties of the target particles in the sample, or alternatively, a fluorescent label affixed to the target particles. The laser is typically a gas laser (such as an Argon or a Helium Neon Laser) or even a diode laser. In the case of fluorescence, each target particle produces a burst of fluorescence photons as it passes through the illumination region. Differentiation of the fluorescence from the illumination or excitation light can be accomplished with a filter or a combination of filters. Detection of the fluorescence is accomplished using a photomultiplier tube or a photodiode. Another technique relies on light scattering of photons in the illumination beam by the target particle. The target particle is identified by its light scattering as a function of the angle of scattering which is a function of its size and shape as well as the wavelength of the scattered photons.

The successful detection and identification of a single target particle depends upon several factors. First, the laser power must be sufficient to generate a large enough number of fluorescence (or, alternatively, scattering) photons during the brief passage of the target particle through the irradiation region. Specifically, it is essential that a sufficient number of photons are generated so that the fluorescent burst from the target particle can be reliably differentiated from random fluctuations in the number of background photons. Second, it is important to minimize these unwanted background photons. These unwanted background photons arise from scattering or from fluorescence emitted by the carrier liquid of the sample or impurities in the liquid, as well as from the apparatus itself, such as the walls of the capillary through which the flow stream passes.

Flow cytometry inherently creates competition between a desirable high flow rate for a reasonable sample throughput in order to provide rapid detection of target particles and high detectivity. High detectivity is predicated upon having a fluorescing (or scattering) target particle in the detection beam long enough to provide a high signal-to-noise detection along with an optical design that will minimize background photons from unwanted scattering and unwanted fluorescence, both of which can dominate system noise. Optimally, a flow cytometer will have a small excitation beam, a high flow rate, and detection optics and associated electronics that allow for the collection of sufficient photons from the target particle to provide high signal-to-noise detection.

Various flow cytometry devices are described in available references. See, for example Flow Cytometry: First Principles, A. L. Givan (1992). Other references include Sage et al. (U.S. Pat. No. 4,660,971); Wu et al. (U.S. Pat. No. 4,661,913); Yamamoto et al. (U.S. Pat. No. 4,786,165); Ohki et al. (U.S. Pat. No. 5,007,732); and Hirako (U.S. Pat. No. 5,135,302). Each of these references also contain references to other relevant publications.

As discussed previously, the competing requirements imposed on flow cytometry create an inherent conflict between high sample throughput and high detectivity that has proven most difficult to overcome resulting in limitations in applications for flow cytometry. In view of the foregoing, it would be an advancement in the art to provide improvements in flow cytometry. It would be another advancement in the art to provide a charge coupled device (CCD) as the detector with the image from the target particle being shifted across the CCD at the same rate that the CCD charge is being shifted across the CCD. It would be an even further advancement in the art to provide a flow cytometer with a time delayed integration (TDI) system to significantly alter the signal-to-noise ratio in favor of detection. Such a novel apparatus and method is disclosed and claimed herein.

BRIEF SUMMARY AND OBJECTS OF THE INVENTION

This invention involves the detection of target particles such as microorganisms, molecules, and the like, using a CCD to provide TDI of the photons from the target particle in the sample stream of the flow cytometer. TDI provides a surprisingly high signal-to-noise ratio of the detection photons by lowering the contribution of photons from unwanted background photons with respect to the photons emitted by the target particle and by lowering the contribution of CCD readout noise. This high signal-to-noise ratio is accomplished by effectively narrowing the field of view thereby reducing the contribution by the background illumination. CCD spectrophotometry can also be used to detect spectra from the target particle to measure the properties of the target particle as well as being able to differentiate between the scattering and fluorescence photons from the target particle. Further, TDI of flow cytometry using a CCD accommodates simultaneous detection and analysis of multiple target particles.

It is, therefore, a primary object of this invention to provide improvements in detection of target particles using flow cytometry.

Another object of this invention is to provide improvements in the method of identifying target particles using flow cytometry.

Another object of this invention is to provide a flow cytometry analysis of target particles with TDI.

Another object of this invention is to use TDI to enhance the signal to noise ratio of a flow cytometry apparatus.

Another object of this invention is to use TDI in combination with a flow cytometry apparatus to provide for the simultaneous detection and analysis of multiple target particles in the sample stream.

Another object of this invention is to coordinate the rate of movement of the image across the CCD during TDI of the CCD with the rate of flow of the target particles in the sample flow.

Another object of this invention is to provide for the facile correlation between the scattering and fluorescence signals from the target particles.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

The invention is best understood from the following description with reference to the drawing wherein like parts are designated by like numerals throughout and taken in conjunction with the appended claims.

General Discussion

A CCD is a solid state device designed to act as an "artificial retina." A dense array of light receptors or pixels are formed over the surface of the CCD. Light striking a pixel creates an electronic charge proportional the intensity or number of photons in the light that strike the pixel during exposure. Conventionally, a CCD image of an object is created by opening a shutter and exposing the CCD to the object. The shutter is then closed and the CCD is read by transferring each charge, row by row, into a serial transport register. After each row transfer, the individual pixels are transferred, one at a time, through an on-chip output amplifier and digitized. The readout and digitization are generally performed as rapidly as possible, restrained only by the existing electronic noise conditions.

The coupling of TDI techniques to a CCD generally requires each row to be shifted more slowly in order to synchronize the pixel shift rate with the rate at which the image (of target particles in the flow stream of the flow cytometer) moves across the CCD. The flow cytometry CCD is not shuttered as described above but is read out on a continuous basis. Image smearing is avoided by moving the image across the CCD at the same rate that the CCD charge is being shifted across the CCD. Accordingly, the charge imposed on each pixel that is read out will have dwelt for an equal period of time on each pixel in one column of the CCD. This means that all of the image pixels read from a single column of the CCD will have been detected with nearly equal quantum efficiency, the mean quantum efficiency of the CCD column.

When used for improving the signal-to-noise ratio for imaging, TDI will permit one to obtain a signal-to-noise many times higher than when using a single detector such as a conventional photomultiplier tube. This means that stray photons from the background are significantly minimized when compared to the overall signal from the target particle. For example, one could use a conventional photomultiplier tube to detect emission from a 1 $\mu$m bacteria in a column of liquid with an illuminated length of 200 $\mu$m and a 50 $\mu$m square cross section. Alternatively, one could use a CCD with 9 $\mu$m square pixels. If a bacterium is contained in a single pixel the background contribution would be reduced by over a factor of more than 100. Clearly, of course, these dimensions and numerical specifications are representative and are provided herein for illustrative purposes only.

The importance of this invention is more clearly understood when one considers the fact that the primary source of noise in a flow cytometer is the high level of laser emission scattered by the carrier fluid, particles in the sample flow, and the components of the flow cytometer itself. A notch filter at the laser line frequency can reduce the intensity of this background scattering by a factor of about $10^{-5}$, but even then the fluorescence from unbound dye molecules (in an immunofluorescence flow cytometer, for example) can readily overwhelm bacterial fluorescence in a single detector flow cytometer. In conventional flow cytometry this problem is addressed by illuminating and collecting light from only a very small region of the flow. On the other hand, TDI achieves the same result without the need to restrict the illuminated volume. A much larger illuminated volume can be used, resulting in a longer residence time for each target particle in the laser beam and a corresponding increased number of collected detection photons.

TDI also allows one to image a small volume of sample flow surrounding an individual target particle without knowing exactly where the target particle resides inside the volume. When the emission of a laser-illuminated flow cell is imaged onto a CCD with the direction and rate of flow aligned with the column direction of the CCD chip, the CCD may be read out at a rate such that the fluorescence emission from a single target particle always accumulates in a single moving charge packet on the CCD chip. Ideally, emitted light from a single target particle will reside in a single pixel.

In the best case, emitted light from the target particle will reside in a single pixel region on the CCD. Accordingly, the benefit of TDI/CCD imaging over a single pixel detector is that the contribution of background photons from scattered light and fluorescence from unbound dye molecules can be decreased by several orders of magnitude, depending on the diameter of the sample stream, the CCD pixel size, and the magnification capability of the system.

Additionally, TDI has benefits over traditional CCD imaging, where multiple short-exposure frames might be used to track a target particle moving through an illuminated flow cell. The CCD and its associated electronics contribute a quantity of noise, called the readout noise, each time a pixel is read from the device. In TDI mode a single pixel, optimally, will follow a single target particle. When the pixel is digitized it will contain one contribution of readout noise. For illustration we assume a readout noise of 100 electrons rms for a single pixel. If non-TDI imaging is used and 100 short-exposure images are used to follow a target particle through the flow and said images are combined by statistical means, the combined contribution from readout noise is the square root of 100×10 electrons rms, or 100 electrons rms. Also, TDI is less computationally intensive than using multiple short-exposure images.

As is apparent from the foregoing, one of the primary requirements for using TDI with CCD flow cytometry is the need to accurately synchronize the TDI with the flow rate in the flow cytometer. A differential between the flow rate and the TDI will result in streaks appearing in the CCD "images." That is, the emitted light from a target particle will extend over many pixels along the column direction of the CCD. The flow rate can be coordinated with the TDI rate using calibration particles in the sample flow. Calibration particles can also be introduced into the flow during the actual experiment as long as the calibration particles have a different emission spectrum than the target particle being detected. Alternatively, sample flow through a capillary will exhibit a parabolic-shaped velocity profile as a result of drag imposed on the liquid stream by the surrounding walls of the capillary which means that one can utilize conventional statistical techniques to coordinate the TDI of the CCD with the flow rate in order to minimize streaks in the CCD images.

The simultaneous detection of two or more different species requires that each species has a unique fluorescing wavelength and/or scattering phase function. Different emission wavelengths can occur due to differences in the intrinsic fluorescence (e.g. autofluorescence or bioluminescence) of the target particles or by tagging them with chemical labels that have differing emission wavelengths. Tagging then allows the use of a TDI/CCD spectrophotometer as a detector that can discriminate between individual target particles and in real time. This means that the individual spectra will be associated with rows of charge packets on the CCD rather than having individual spots (associated with single charge packets on the CCD) shifted down the CCD in the TDI imaging mode.

Further, since a CCD can be binned, i.e., a rectangular grouping or "bin" of pixels can be read out as a single superpixel with a single contribution of readout noise thereby meaning that the spectral resolution of the CCD can be changed to meet the problem encountered, while minimizing readout noise. Binning also allows for faster CCD readout, with the readout speed being approximately proportional to the binning factor. For example, if the CCD is binned by a factor of ten along the row dimension the CCD can be read out approximately ten times faster. This means that for a single-species detection, a 768×512 CCD can be read out as a 768×1 device thereby providing for an increase in readout speed of approximately 500.

Flow Cytometry Flow Rate Considerations

Conventionally, the core diameter or cross sectional area of the irradiation zone of the flow cytometer determines the volume of the background solution illuminated by the laser and, therefore, viewed by the detection system. The rate of solution flow through this irradiation zone determines the length of time the target particle is being irradiated by the laser beam. This is referred to as the transit time. Transit time is important because the residual, unbound fluorescent tag in the observed volume of solution contributes to the number of background photons collected by the detection system. Accordingly, a large number of background photons can reduce the signal-to-noise ratio to such a degree as to render detection of the target particle impossible. This means that the core diameter and the transit time jointly determine the signal-to-noise ratio for the detection of the target particle.

The critical parameter that affects the transit time is the flow rate of the solution through the irradiation zone. This parameter is typically designated as the core volumetric flow rate, q, in milliliters per second, ml/s, and is related to the cross sectional area of the irradiation zone, A, in square centimeters, $cm^2$, along with the flow velocity, v, in centimeters per second, cm/s. Accordingly the cross sectional area, A, can be expressed as $A=q/v$. If the irradiation zone is circular then its diameter, d, in micrometers, can be calculated using the equation $d=1.13\times10^{-4} (q/v)^{1/2}$.

As discussed earlier, the time required to read one line of the CCD chip determines the flow rate because the TDI measurement requires the sample flow to be synchronized as closely as possible with the charge transfer on the CCD chip. One low-cost CCD camera that has TDI and binning implemented in software uses a CCD chip with 9 $\mu$m square pixels and can be read out at a rate corresponding to a maximum flow rate of 25 cm/s (assuming an image magnification of one). Consideration of the simultaneous needs for spectral dispersion (i.e., approximately 50 spectral elements) and lateral binning on the CCD chip suggests an optimal core diameter of 50 $\mu$m (for this particular example). Thus, the core volumetric flow rate for these conditions is calculated to be $5\times10^{-4}$ ml/s. This is a key quantity because it determines the total analysis time. For example, if the sample has a volume of one ml, the total analysis time is predicted to be 2,000 seconds.

However, I anticipate that my novel TDI/CCD flow cytometer will provide several improvements that will significantly decrease the analysis time:

1. Image Demagnification

Since the TDI approach provides an improvement in the signal-to-noise ratio of about 100 times over traditional flow cytometry, image demagnification can be used to lengthen the time that a target particle will be detected on a given pixel. Assuming a demagnification of 10, the maximum flow rate of 25 cm/s from our discussion, above, becomes 250 cm/s. This then decreases the analysis time for a fixed flow volume by a factor of 10. While this approach also degrades the signal-to-noise ratio it is practical due to the improved signal-to-noise ratio achieved through my novel TDI approach.

2. Increased Core Diameter

If the image is demagnified by a factor of 10, then the core diameter can be increased to about 90 $\mu$m (for a CCD chip with 9 $\mu$m pixels). Compared with a 50 $\mu$m core diameter, this increases the sample volumetric flow rate by a factor of 3.2. Accordingly, the foregoing analysis time is decreased from 2,000s to 625s.

3. Faster CCD Readout

A CCD camera that has read rates that are a factor of 10, or more, faster than the nominal read rate of 160 kHz can decrease the analysis time by an additional factor of 10, or more.

4. Decreased Spectral Resolution

A two-color scheme for simultaneous detection of two species is possible. For example, using a spectral resolution of 50 pixels (i.e., 512 lateral pixels binned to 50), would provide adequate spectral dispersion to resolve the two emission bands. The CCD can be binned to match the number of different types of target particles, e.g., using only four spectral elements, one for each emission band and two for the background signal. This change in spectral resolution by a factor of 10 changes the read time by a factor of about 10 which decreases the analysis time accordingly.

Clearly, of course, these four changes would not provide an aggregate decrease in the analysis time of 3,200 times. In particular, these changes either decrease the transit time of the target particle or increase the background noise which degrades the signal-to-noise ratio. However, one does have the latitude to increase the analysis speed by at least an order of magnitude and still have an order of magnitude increase in the signal-to-noise ratio over a conventional flow cytometer. Accordingly, I presented the above discussion to illustrate the point that the projected sampling time can be reduced by at least an order of magnitude.

Importantly, although I have focused this discussion of the use of TDI for the detection of target particles such as microorganisms using fluorescent labels, this novel discovery is not limited to microorganisms or to fluorescent measurements. For example, this same technique can be applied to the detection of single molecules through fluorescence or absorption spectroscopy in a flow cytometer. This is possible because TDI significantly enhances the signal-to-noise ratio of the detector by decreasing the contribution of the background component from the surrounding medium. Examples of such molecular analysis are the presence of explosive molecules or groundwater contaminant molecules, e.g. benzene, trichloroethylene, etc.

Detailed Description

Figure 1:
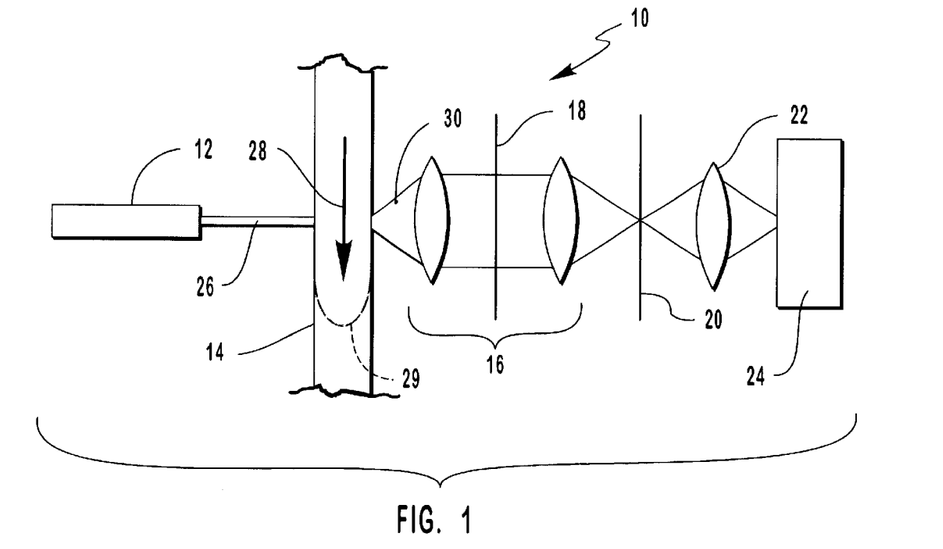
FIG. 1 is a schematic of a first embodiment of an imaging TDI/CCD flow cytometry apparatus of this invention.

Referring now to FIG. 1, a first preferred embodiment of the novel TDI/CCD flow cytometer of this invention is shown generally at 10 and includes a laser 12, a flow zone 14 having a sample flow 28 passing therethrough, reimaging optics 16 having a notch filter 18 therein, an aperture 20, a focus lens 22 and a CCD 24. Laser 12 emits a laser beam 26 through flow zone 14 to illuminate a first target particle 32 and a second target particle 33 (FIG. 2) therein and to cause the same to fluoresce as fluorescence 30. Fluorescence 30 is optically processed by reimaging optics 16 and notch filter 18 and focused onto a field-of view aperture 20. Focus lens 22 focuses the resultant fluorescence 30 onto CCD 24 (FIG. 3) as will be discussed more fully hereinafter.

Sample flow 28 passes through flow zone 14 and exhibits a typical, parabolic-like flow velocity profile 29 as shown schematically herein by the dashed line in flow zone 14. Flow velocity profile 29 is created as a result of the surface drag phenomena imparted to the liquid of sample flow 28 by the wall surface of flow zone 14. This is an inherent feature of any liquid stream flowing through a conduit and can be readily eliminated by the conventional technique of enclosing sample flow 28 in a sheath of moving air or liquid (not shown) to thereby create what is commonly referred to as a "sheath flow."

Figure 2:
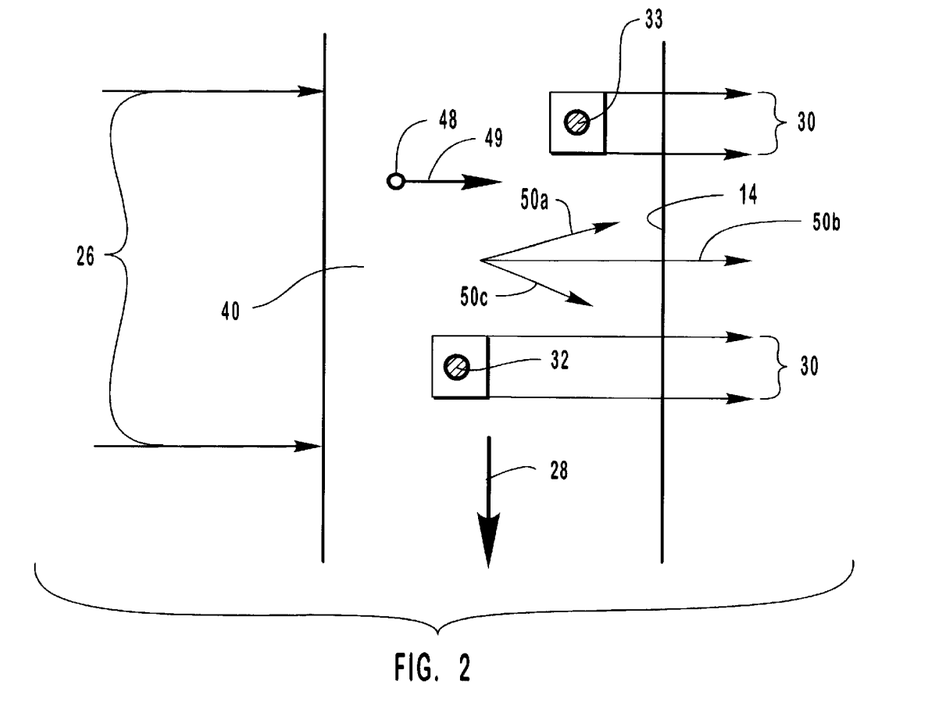
FIG. 2 is an enlarged, schematic illustration of two target particles in the core flow of the TDI/CCD flow cytometer of FIG. 1 as they pass through the excitation zone of a laser beam.

Referring now also to FIG. 2, flow zone 14 with an irradiation zone 40 shown therein is shown greatly enlarged for ease of illustration. For example, laser beam 26 is shown as a 200×50 μm laser beam illuminating flow zone 14 which is shown as 50 μm diameter sample stream having a cylindrical cross section. A first target particle 32 is shown in sample flow 28 toward the lower end of irradiation zone 40 while a second target particle 33 is shown entering the upper end of irradiation zone 40. A calibration particle 48 is also included in sample flow 28 for the purpose of allowing the operator (not shown) to suitably calibrate TDI/CCD flow cytometer 10 as will be discussed more fully hereinafter. Calibration particle 48 emits a calibration photon 49 when illuminated by laser beam 26.

Figure 3:
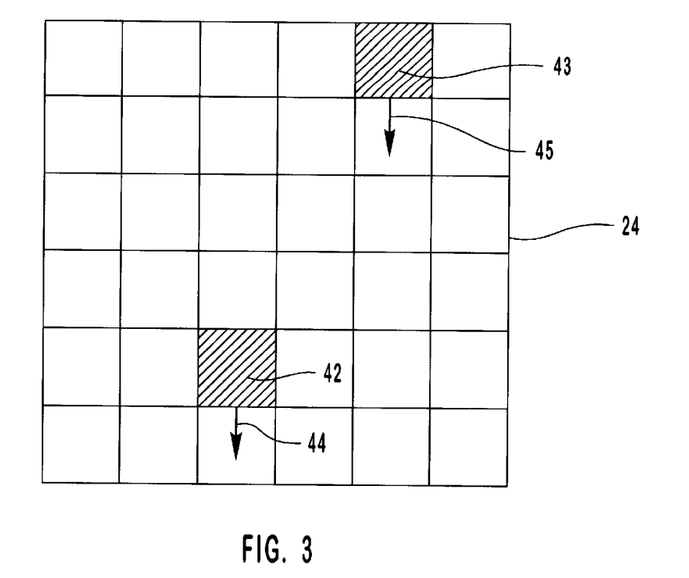
FIG. 3 is an enlarged schematic illustration of the face of a CCD illustrating the charge shift on the CCD at the same velocity as the flow velocity of the target particles.

Referring now also to FIG. 3, a greatly enlarged, schematic of a portion of CCD 24 is shown. Two shaded areas are shown as first pixel 42 and second pixel 43 which represent fluorescence 30 from first target particle 32 and second target particle 33, respectively. First movement arrow 44 on first pixel 42 represents the movement or transfer of first pixel 42 across the face of CCD 24. Correspondingly, second movement arrow 45 on second pixel 43 represents the movement or transfer of second pixel 43 across the face of CCD 24. Importantly, the rate of movement of first movement arrow 44 and second movement arrow must be nearly identical to that of sample flow 28 as imaged onto CCD 24 in order to minimize streaking of the digitized image obtained by CCD 24. The image of calibration particle 48 is not illustrated on CCD 24 for purposes of simplicity although it would be essentially identical to that of either first pixel 42 or second pixel 43.

Referring to all of FIGS. 1–3, sample flow 28 passes through flow zone 14 carrying target first particle 32 and second target particle 33 therein along with an occasional calibration particle 48. Laser 12 illuminates first target particle 32, second target particle 33, and calibration particle 48 with laser beam 26 as they each pass through irradiation zone 40 thereby causing first target particle 32, second target particle 33, and calibration particle 48 to fluoresce due to intrinsic fluorescence (e.g. autofluorescence or bioluminescence) or due to being tagged with chemical labels that have characteristic emission wavelengths. Alternatively, first target particle 32, second target particle 33, and calibration particle 48 can cause characteristic scattering of laser beam 26. In any event, each of first target particle 32, second target particle 33, and calibration particle 48 emit specific illumination which is referred to herein as fluorescence 30 for sake of simplicity or fluorescence 49 in the case of calibration particle 48. Fluorescence 30 along with fluorescence 49 is optically processed in reimaging optics 16 containing a notch filter 18 therein. Notch filter 18 provides a filtering function by filtering out a significant portion of any background scattering caused by laser beam 26 generating scattering 50 from the carrier fluid of sample flow 28 and even from the sidewalls of flow zone 14, itself. Scattering 50 is shown as having a plurality of scattering rays 50a–50c which, in the absence of notch filter 18, would be picked up by reimaging optics 16 and directed to CCD 24. As it is presently constructed, notch filter 18 strongly attenuates light at the wavelength of laser beam 26 while permitting light of the wavelengths of fluorescence 30 and fluorescence 49 to pass. This is an important feature in flow cytometry since scattering rays 50 are noise which could significantly overwhelm the signal from first target particle 32 and second target particle 33 as well as from calibration particle 48.

Fluorescence 30 is directed through aperture 20 by reimaging optics 16 and focused by focus lens 22 onto CCD 24. In CCD 24, fluorescence 30 from first target particle 32 is recorded as first pixel 42 while fluorescence 30 from second target particle 33 is recorded as second pixel 43. First target particle 32 traverses flow zone 14 in sample flow 28 while first pixel 42 traverses the face of CCD 24 at (ideally) an identical rate of travel (assuming an image magnification of unity) as shown by first movement arrow 44. Correspondingly, second pixel 43 representing second target particle 33 moves across the face of CCD 24 at the same rate of travel as second target particle 33 in sample flow 28 and as shown by second movement arrow 45.

As set forth previously, sample flow 28 (in a flow zone 14 versus a sheath flow (not shown)) has a flow velocity profile 29. As such, the distance of each of first target particle 32, second target particle 33, and calibration particle 48 from the axis of sample flow 28 will be represented by a differential in the velocity of flow of the respective particle. Accordingly, the rates of movement of first movement arrow 44 and second movement arrow 45 will be different as a result of the spatial separation of the respective target particle, first target particle 32 and second target particle 33, from the side wall of flow zone 14. Accordingly, this differential in the rates of movement of first target particle 32 and second target particle 33 will result in streaking of one or both of their images as recorded on CCD 24 as first pixel 42 and second pixel 43, respectively. However, by the application of relatively straight-forward statistical analysis techniques one can readily compensate for this flow phenomena caused by flow velocity profile 29. Further, one can use this same statistical analysis tool to provide a method for determining the rate of flow for a majority of first target particle 32 and second target particle 33 in flow stream 28 to thereby effectively control the rate of transfer of first pixel 42 and second pixel 43, respectively, across the face of CCD 24. This technique would be an effective way to eliminate the requirement for the use of calibration particle 48. Streaking of first pixel 42 or second pixel 43 is a relatively minor problem since a substantial portion of the flow of sample flow 28 is at or near the axis of flow as can be seen from flow velocity profile 29. Thus, while flow at the wall will have zero velocity, one can set the charge transfer rate on CCD 24 by measuring the streak length of target particles near the axis of the flow. The enhancement of the signal-to-noise of fluorescence 30 through TDI results in a corresponding diminution of the effect of the signal from scattering ray 50b, particularly since scattering rays 50 tend to be distributed throughout sample flow 28 whereas fluorescence 30 is localized which results in a very low amount of signal from scattering ray 50b being recorded by CCD 24 in the same pixel, first pixel 42 or second pixel 43, as representative of the respective target particle, first target particle 32 or second target particle 33.

Figure 4:
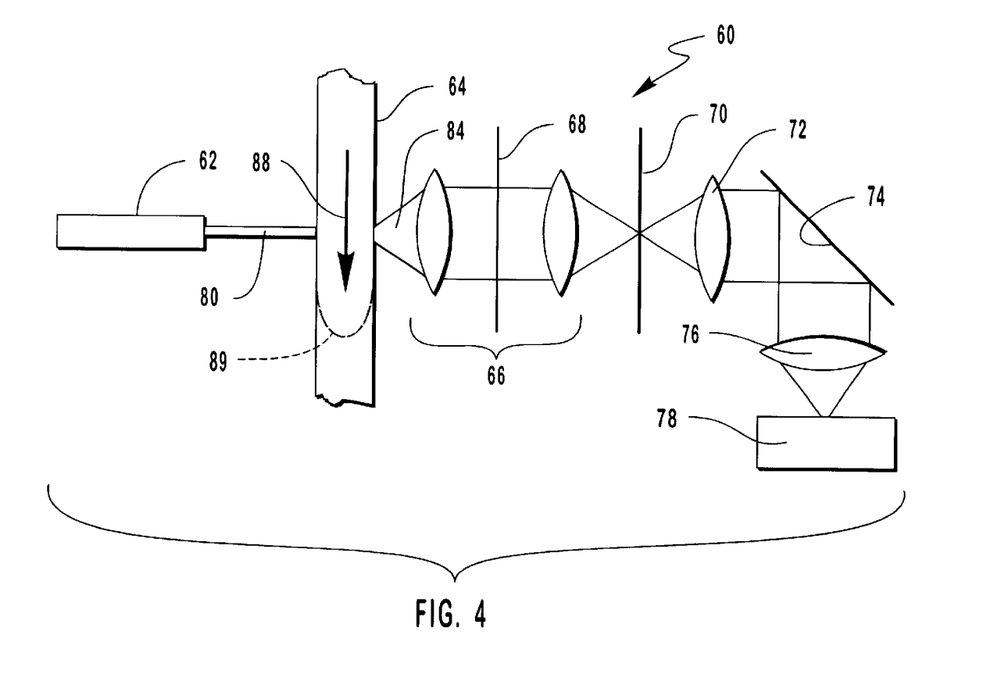
FIG. 4 is a schematic of a second embodiment of a TDI/CCD flow cytometry apparatus of this invention for detecting two or more target particles having different emission spectra.

Referring now to FIG. 4, a second embodiment of my novel TDI/CCD flow cytometer is shown generally at 60 and includes a laser 62, a flow zone 64, reimaging optics 66 with a notch filter 68 therein, a slit 70, a collimator 72, a grating 74, a focusing lens 76, and a CCD 78. Laser 62 directs a laser beam 80 through flow zone 64 causing a first target particle 82 and a second target particle 83 (FIG. 5) to fluoresce or otherwise emit fluorescence photons 84. Fluorescence photons 84 are optically processed through imaging optics 66 and notch filter 68 and are focused through aperture slit 70 and then collimated by collimator 72 and directed against grating 74. Grating 74 is designed to separate different wavelengths of fluorescence photons 84 prior to directing the same to CCD 78 as will be discussed more fully hereinafter.

Sample flow 88 also includes a flow velocity profile 89 similar to flow velocity profile 29 (FIG. 1) so that the discussion thereof would be identical to that previously discussed, particularly with respect to using statistical analysis of sample flow 88 as a means for calibrating the readout of CCD 78.

Figure 5:
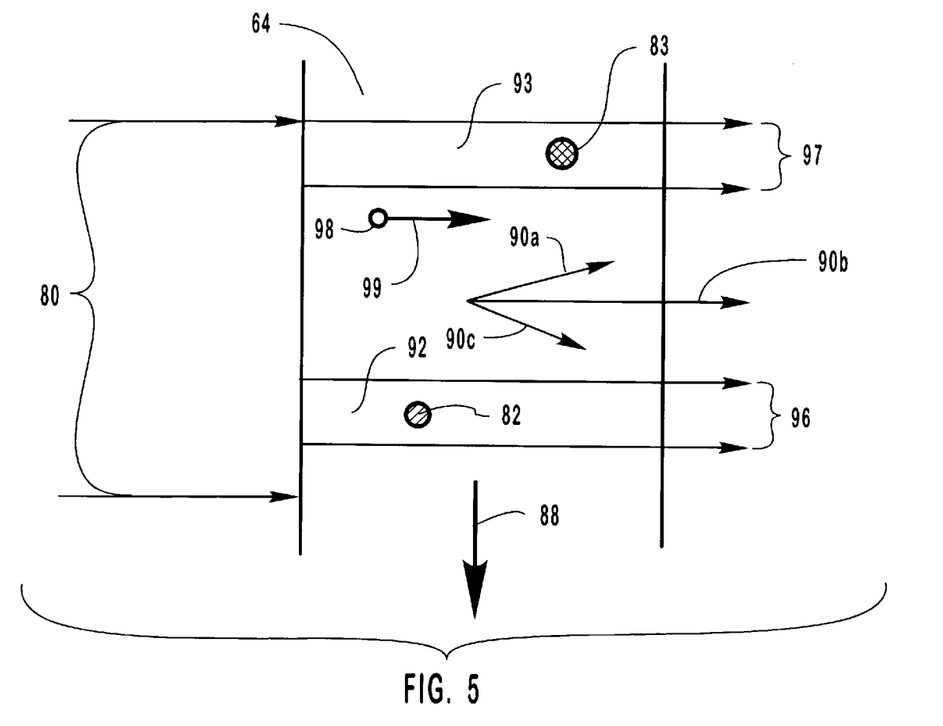
FIG. 5 is an enlarged, schematic illustration of two target particles having different emission spectra passing through the flow zone of the TDI/CCD flow cytometer of FIG. 4.
Figure 6:
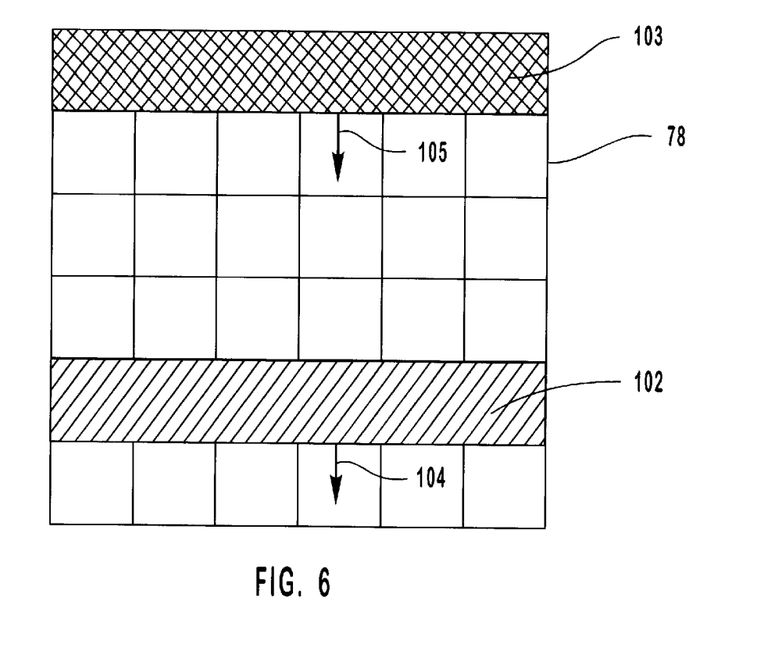
FIG. 6 is an enlarged schematic illustration of the face of a CCD illustrating the charge shift on the CCD from the two target particles of FIG. 5.

Referring now to FIGS. 5 and 6, a portion of flow zone 64 is shown greatly enlarged and as having two different types of target particles therein, first target particle 82 and second target particle 83. Flow zone 64 is illuminated by laser beam 80 which causes first target particle 82 to emit a first fluorescence 96 and second target particle 83 to emit a second fluorescence 97 as well as a scattering fluorescence 90a–90c. In this particular embodiment of TDI/CCD flow cytometer 60, a first band 94 across flow zone 64 and containing first target particle 82 is read by CCD 78 as a first spectrum 102 while a second band 95 across flow zone 64 and containing second target particle 83 is read by CCD 78 as a second spectrum 103.

Sample flow 88 also includes a calibration particle 98 which emits a calibration photon 99 when illuminated by laser beam 80. Calibration particle 98 allows the operator (not shown) of TDI/CCD flow cytometer 60 to calibrate the operation of CCD 78 to the flow rate of sample flow 88 as will be discussed therein before with respect to target particle 48 (FIG. 2).

First spectrum 102 moves across the face of CCD 78 at a rate illustrated schematically by first movement arrow 104 while second spectrum 103 moves across the face of CCD 78 at a rate illustrated schematically by second movement arrow 105. The rate of travel of first movement arrow 104 and second movement arrow 105 are each carefully coordinated with the rate of travel of sample flow 88 as determined through the use of calibration particle 98. This is readily accomplished by detecting calibration photon 99 on CCD 78 and coordinating its rate of movement across CCD with that of sample flow 88.

First spectrum 102 is shown having a particular cross hatch while second spectrum 103 is shown with a different cross hatch to illustrate that the spectra, first spectrum 102 and second spectrum 103, have emissions at different wavelengths since first target particle 82 is a different species from that of second target particle 83. Further, the location of first target particle 82 can be at any position inside first target zone 92 while the location of second target particle 83 can be at any position inside second target zone 93 since both first target zone 92 and second target zone 93 are read out as first fluorescence 96 and second fluorescence 97, respectively. First fluorescence 96 is recorded by CCD 78 as first spectrum 102 while second fluorescence 97 is recorded by CCD as second spectrum 103.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. Apparatus for identifying particles in a sample stream moving through a flow zone at a rate relative to the flow zone, the sample stream containing target particles, the apparatus comprising:
   means for illuminating the sample stream within the flow zone;
   a detector for detecting light emitted or scattered from illuminated target particles within the flow zone;
   a time delayed integration element for integrating the detected light, the time delayed integration synchronized to the sample stream flow rate; and
   means for identifying target particles responsive to the time delayed integration element.

2. The apparatus of claim 1 wherein the sample stream is contained in a flow cytometer.

3. The apparatus of claim 1 wherein the illuminating means comprises a laser.

4. The apparatus of claim 1 wherein the detector comprises a charge coupled device (CCD).

5. The apparatus of claim 4, wherein the time delayed integration element includes means for shifting CCD pixel rows in synchronization with the sample stream flow rate.

6. The apparatus of claim 5 wherein the means for identifying target particles includes means for reading pixels the CCD one row at a time.

7. The apparatus of claim 5 wherein the means for identifying target particles includes means for applying statistical analysis to data collected by the pixels of the CCD to determine pixels related to a single target particle.

8. The apparatus of claim 1, further including means for measuring the sample stream flow rate including:

a calibration particle in the sample flow; and means for measuring the velocity of the calibration particle.

9. The apparatus of claim 8, wherein the sample stream rate is measured in real time while target particles are being detected.

10. The apparatus of claim 8 wherein the calibration particle is a target particle.

11. The apparatus of claim 10, wherein the sample stream rate is measured in real time while target particles are being detected.

12. The apparatus of claim 1, further including means for measuring the sample stream flow rate including:

means for applying statistical analysis to data collected by pixels of the CCD to determine pixels related to a single target particle; and means for measuring velocity of at least one target particle.

13. The apparatus of claim 1, further including means for synchronizing the time delayed integration element and the sample stream flow rate by adjusting the time delayed integration element until target particles appear substantially as dots.

14. The apparatus of claim 1, further including means for detecting two different target particle species, wherein each species produces a unique frequency or phase shift in its scattered or emitted light, wherein the detector includes means for differentiating frequency of phase shift.

15. The apparatus of claim 1, further including a notch filter between the sample stream and the detector for filtering out undesired light.

* * * * *

UNITED STATES PATENT AND TRADEMARK OFFICE
CERTIFICATE OF CORRECTION

PATENT NO. : 6,256,096 B1
DATED : July 3, 2001
INVENTOR(S) : Johnson et al.

It is certified that error appears in the above-identified patent and that said Letters Patent is hereby corrected as shown below:

<u>Column 3,</u>
Line 50, delete "restrained" and insert -- constrained --;

<u>Column 4,</u>
Line 13, delete "over";
Line 65, before "square" insert -- ( --;
Line 65, after "100" insert -- ) --;

<u>Column 8,</u>
Line 11, delete "target";
Line 11, after "first" insert -- target --;

<u>Column 9,</u>
Line 60, delete "94" insert -- 92 --;
Line 62, delete "95" insert -- 93 --;

<u>Column 10,</u>
Line 40, before "rate" insert -- flow --;
Line 62, before "the" insert -- of --;
Line 64, delete "5" insert -- 6 --;

<u>Column 11,</u>
Line 17, before "pixels" insert -- the --; and

<u>Column 12</u>
Line 13, delete "of" insert -- or --.

Signed and Sealed this

Sixteenth Day of July, 2002

*Attest:*

*Attesting Officer*

JAMES E. ROGAN
*Director of the United States Patent and Trademark Office*